(12) United States Patent
Sugita et al.

(10) Patent No.: US 6,326,192 B1
(45) Date of Patent: *Dec. 4, 2001

(54) VECTOR FOR GENE TRANSFER INTO PLANT ALLOWING OPTIONAL DELETION OF MARKER GENE

(75) Inventors: Koichi Sugita; Mikiko Uesugi; Etsuko Matsunaga; Hiroyasu Ebinuma, all of Tokyo (JP)

(73) Assignee: Nippon Paper Industries Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/147,241

(22) PCT Filed: May 9, 1997

(86) PCT No.: PCT/JP97/01569

§ 371 Date: Nov. 9, 1998

§ 102(e) Date: Nov. 9, 1998

(87) PCT Pub. No.: WO97/42334

PCT Pub. Date: Nov. 13, 1997

(30) Foreign Application Priority Data

May 9, 1996 (JP) ..................................................... 8-115114
Mar. 31, 1997 (JP) ..................................................... 9-080821

(51) Int. Cl.[7] .......................... C12N 15/82; C12N 15/84; C12N 15/90

(52) U.S. Cl. .................. 435/320.1; 435/69.1; 435/468; 435/469; 800/288; 800/290; 800/295

(58) Field of Search ................................. 435/320.1, 69.1, 435/410, 419, 468, 469; 536/24.1; 800/278, 288, 290, 295

(56) References Cited

U.S. PATENT DOCUMENTS 5,965,791 * 10/1999 Ebinuma et al. ..................... 800/278

FOREIGN PATENT DOCUMENTS

WO93/01294 * 1/1993 (WO) ............................. C12N/15/82

OTHER PUBLICATIONS

Dale et al, Proc. Natl. Acad. Sci, USA, vol. 88, pp. 10558–10562, 1991.*
Lyznik et al, Plant J., vol. 8, pp. 177–186, 1995.*
Smigocki et al, Proc. Natl. Acad. Sci. USA, vol. 85, pp. 5131–5135, 1988.*

(List continued on next page.)

Primary Examiner—Gary Benzion
Assistant Examiner—Ashwin Mehta
(74) Attorney, Agent, or Firm—Oblon, Spivak, McClelland, Maier & Neustadt, P.C.

(57) ABSTRACT

The present invention relates to a vector for introducing a desired gene into a plant, wherein a selectable marker gene introduced into a plant cell along with a desired gene is optionally removable from the DNA such as chromosome or the like where it exists and functions, then disappeared the function thereof after its expression, and the expression of the selectable marker gene and the disappearance of the function thereof are detectable by morphological change of the tissue derived from the plant cell into which the selectable marker gene is introduced. Also, the present invention constitutes a vector using a morphological abnormality induction gene as a selectable marker gene, while putting a removable DNA element under control of an inducible promoter, wherein the morphological abnormality induction gene is positioned such that it behaves integrally with the removable DNA element, and wherein a desired gene is positioned such that it does not behave integrally with the removable DNA element.

8 Claims, 15 Drawing Sheets

OTHER PUBLICATIONS

Smigocki, A. C., Plant Mol. Biol., vol. 16, pp. 105–115, 1991.*

Donald et al, EMBO J., vol. 9, pp. 1717–1726, 1990.*

WO, 93/01283, A1 (The United States of America as Represented by the Secretary of Agriculture), Jan. 21, 1993.

The Plant Cell, vol. 1, (1989), A. Spena et al., "Cell–Autonomoous behavior of the rolC Gene of *Agrobacterium rhizognes* during Leaf Development:: A Visual Assay for Transposon Excision in Transgenic Plants", pp. 1157–1164.

* cited by examiner

VECTOR FOR GENE TRANSFER INTO PLANT ALLOWING OPTIONAL DELETION OF MARKER GENE

TECHNICAL FIELD

The present invention relates to a novel vector for introducing a desired gene into a plant using genetic engineering methods to obtain a transgenic plant.

BACKGROUND ART

Transformation of microorganisms and cultured cells using genetic engineering is currently applied to the production of physiologically active substances useful as medicines and the like, and thus greatly contributes to the industry. In the field of plant breeding, industrial application of genetic engineering lags behind because the life cycles of plants are much longer than those of microorganisms and the like. However, since this technology enables a desired gene to be directly introduced into plants to be bred, it has the following advantages compared to classical breeding which requires multiple crossing: (a) it is possible to introduce only a characteristic to be improved; (b) it is possible to introduce characteristics of species other than plants (such microorganisms and the like); and (c) it is possible to greatly shorten the breeding period. Thus, genetic engineering methods for plant breeding have been investigated vigorously.

Specifically, the production of transgenic plants requires the following three steps: (1) introducing the desired gene into the plant cell (including introduction of the same into the chromosomes, nucleus and the like); (2) selecting plant tissue made only of cells into which the desired gene has been introduced; and (3) regenerating a plant from the selected plant tissue. Furthermore, among these, in selecting the tissue into which the desired gene has been introduced, a selectable marker gene is generally used. In other words, generally, a selectable marker gene is introduced into plant cells along with a desired gene, and a characteristic feature shown by expression of the selectable marker gene in the introduced cells, as well as a tissue derived from the cells, is used as an index for the introduction of the desired gene. Consequently, a selectable marker gene is introduced and expressed in addition to a desired gene in almost all cases of the plants so far transformed by means of genetic engineering methods.

However, with regard to the products of genes used as such selectable markers, their safety to the human body has been confirmed only on few genes. Accordingly, even if tomatoes or potatoes are produced by introducing a useful character using a selectable marker gene, it will entail many obstacles, including a vague unrest in consumers, when they are provided as edible products so long as the selectable marker gene is expressed.

Furthermore, after selection of a gene-introduced tissue, expression of a selectable marker gene will cause considerable obstacles even at the level of researchers studying on the plant breeding. That is, when a transgenic plant which has been produced by using a selectable marker gene is again introduced by another gene, introduction of the gene cannot be carried out using the same selectable marker gene. In other words, since the selectable marker gene has been already present in the plant, the selectable marker gene is always expressed in the plant whether or not the new desired gene is introduced into the plant along with the selectable marker gene. Therefore, such a selectable marker gene can no longer be used as an index of the introduction of the new desired gene. Consequently, the number of times of repeated gene transfer into a certain plant is naturally restricted by the number of different selectable marker genes useful in the plant. However, kinds of selectable marker genes so far available are not so many. Additionally, all of the selectable marker genes are not necessarily useful in the plant of the object.

For resolving the above-described problems and thereby efficiently producing a gene-introduced tissue or plant completely free from the influence of a selectable marker gene, the present inventors have already developed a novel vector for introducing a desired gene into plant cells (Japanese Patent Application No. H07-313432). This vector comprises a desired gene, a morphological abnormality induction gene as a selectable marker gene, and a removable DNA element, wherein the morphological abnormality induction gene is positioned such that it behaves integrally with the removable DNA element, and wherein the desired gene is positioned such that it does not behave integrally with the removable DNA element. When a desired gene is introduced into a plant using this vector, the selectable marker gene is removable from the DNA where it exists and functions, then disappeared the function thereof at a certain ratio after its expression through cultivation of transgenic cells, and the expression of the selectable marker gene and the disappearance of the function thereof can be detected by morphological change of the tissue derived from the plant cell into which the selectable marker gene is introduced. That is, a tissue derived from the cell in which this selectable marker gene is expressed shows a certain abnormal morphology, and, when cells from which the function of the selectable marker gene is disappeared by the removal thereof (in other words, cells into which only the desired gene is introduced) are generated from the tissue thereafter, a tissue having normal morphology is regenerated from the resulting cell. Accordingly, by using this vector, a plant tissue comprising cells into which only a desired gene is introduced, as well as its subsequent plant individual, can be produced by simply repeating culturing of the gene-introduced cells and selection of tissues obtained by the culturing visually.

However, the removal of the selectable marker gene could not be freely controlled even in this vector developed by the present inventors. Accordingly, if the ability of the removable DNA element is high, the selectable marker gene will be removed very quickly. For example, the selectable marker gene will be removed immediately after its introduction into plant cells along with a desired gene and before its expression. In this case, a tissue constituted by cells into which only the desired gene is introduced may be obtained; however, the selectable marker gene-induced morphological changes of the gene-introduced tissue do not occur and, as the result, such a tissue cannot be selected.

Additionally, if the removal of the selectable marker gene can be freely controlled, the generation of cells into which only a desired gene is introduced and the generation of plant tissues derived from such cells can be synchronized or appropriately controlled, and therefore, it will be very convenient in actually producing a transgenic plant using such a vector.

Consequently, an object of the present invention is to provide a vector for introducing a gene into a plant, which contains a selectable marker gene, in which functions of the selectable marker gene introduced into plant cells together with a desired gene can be optionally removable after its expression by removing the selectable marker gene from DNA, such as chromosomal or the like, where it exists and functions and the expression and disappearance of the function of the selectable marker gene can be detected by the morphological changes of tissues derived from the gene-introduced plant cells.

DISCLOSURE OF THE INVENTION

The object of the present invention can be accomplished by constructing a vector using a morphological abnormality induction gene as a selectable marker gene, while putting a removable DNA element under control of an inducible promoter, wherein the morphological abnormality induction gene is positioned such that it behaves integrally with the removable DNA element, and wherein a desired gene is positioned such that it does not behave integrally with the removable DNA element.

The present invention will be discussed below in detail.

As used therein, the morphological abnormality induction gene is a gene that induces into a tissue of a plant morphologically abnormal differentiation such as a dwarf, destruction of apical dominance, change in pigments, formation of a crown gall, formation of hairy roots, waving of the leaves or the like. It is reported that various morphological abnormality induction genes, such as cytokinin synthesis genes (e.g., ipt (isopentenyltransferase) gene (A. C. Smigocki, L. D. Owens, *Proc. Natl. Acad. Sci. USA*, 85:5131, 1988)), iaaM (tryptophan monooxygenase) gene (H. J. Klee et al., *GENES & DEVELOPMENT*, 1:86, 1987), gene 5 (H. Koerber et al., *EMBO Journal*, 10:3983, 1991), gene 6b (P. J. J. Hooyaas et al., *Plant Mol. Biol.*, 11: 791, 1988), rol genes such as rolA to D (F. F. White et al., *J. Bacteriol.*, 164:33, 1985) and the like, are present in bacteria of the genus Agrobacterium or the like that induce tumor or teratoma in various plants (that is, formation of adventitious shoots or adventitious roots). Furthermore, an iaaL (indoleacetic acid-lysine synthetase) gene in *Pseudomonas syringae* subsp. savastanoi (A. Spena et al., *Mol. Gen. Genet.*, 227:205, 1991), and homeo box genes, phytochrome genes and the like in various plants are reported.

Any of these genes can be used in the present invention. Among these, the ipt gene which induces destruction of apical dominance and the rol genes which induces the formation of hairy roots, dwarf, waving of the leaves and the like of a plant regenerated from the hairy root are preferable selectable marker genes in the present invention because they induce characteristic morphological abnormality among various morphological abnormality induction genes.

Furthermore, one can design a combination of these selectable marker genes, so that a specific structure, such as an adventitious shoot, an adventitious root or the like is redifferentiated in a specific plant into which these selectable marker genes are introduced. In the present invention, such a combination of morphological abnormality induction genes can be used, according to the conditions of producing the transgenic plant, such as the kind of a plant into which the genes are to be introduced.

As used herein, a removable DNA element is an element of a DNA sequence which itself is removable from the DNA wherein the DNA element exists and functions. In plants, a transposon present in a chromosome is known as this element. The structure, activity and behavior of transposons have been almost completely identified. For the transposon to function, two components are required in principle, an enzyme which is expressed from the gene present therein and which catalyzes the excision and transposition of the transposon itself (transposase), and DNA binding sequences which are present in the terminal region of the transposon and upon which the transposase acts. By these elements, the transposon is excised from the chromosome in which it exists, and is then usually transposed to a new position in the DNA. However, at a certain ratio, the transposon also disappears without being transposed. The present invention makes use of such a transposition error of the transposon.

The transposon can be of one of two types, either an autonomous transposon or a non-autonomous transposon. The autonomous transposon maintains the two elements, the transposase and the DNA binding sequence. In the autonomous transposon, the transposase is expressed and binds to the DNA binding sequence for action, whereby the transposon is autonomously excised from the chromosome. The non-autonomous transposon retains the terminal DNA binding sequence to which the transposase is bound for action. In the non-autonomous transposon, the transposase gene undergoes mutation such that the transposase is not expressed; thus the transposon cannot be excised from the chromosome autonomously. However, when transposase is supplied to the non-autonomous transposon from the autonomous transposon or from an independent transposase gene, the non-autonomous transposon behaves similarly to the autonomous transposon.

Accordingly, in the present invention, both the autonomous and non-autonomous transposons can be used. For example, a non-autonomous transposon can be used by inserting therein a morphological abnormality induction gene and a transposase gene which is obtained from an autonomous transposon or synthesized.

Examples of the autonomous transposons include Ac and Spm isolated from maize (A. Gierl and H. Saedler, *Plant Mol. Biol.*, 19:39, 1992). Ac can be obtained by digesting wx-m7 locus in the chromosome of the maize with restriction endonuclease Sau3A (U. Behrens et al., *Mol. Gen. Genet.*, 194:346, 1984). This autonomous transposon is the most analyzed among plant transposons. In fact, the DNA sequence has already been determined (M. Mueller-Neumann et al., *Mol. Gen. Genet.*, 198:19, 1984). Also, examples of non-autonomous transposons include Ds and dspm obtained by deleting the inner regions of Ac and Spm, respectively (H.-P. Döring and P. Starlinger, *Ann. Rev. Genet.*, 20:175, 1986) and those isolated from many plants, other than maize, such as snapdragon, morning glory and the like (for example, Y. Inagaki et al., *Plant Cell*, 6:375, 1994). When these transposons are introduced into chromosomes of exogenous plants, these transposons are also excised from a chromosome and transposed (for example, B. Baker et al., *Proc. Natl. Acad. Sci. USA*, 83:4844, 1986).

Another removable DNA element, which is not present in plants, is an element derived from a site-specific recombination system. A site-specific recombination system consists of two elements, a recombination site (corresponding to the removable DNA element of the present invention) having a characteristic DNA sequence, and an enzyme (recombinase) that binds to the DNA sequence specifically and catalyzes the recombination between these DNA sequences if two or more of the sequences exist. When the two DNA sequences are oriented in the same direction at a given interval on the same DNA molecule, the region held by these DNA sequences is excised from the DNA molecule, such as a plasmid, chromosome or the like. When the two DNA sequences are oriented in opposite directions on the same DNA molecule, the region held by these DNA sequences is inverted. The present invention utilizes the former excision. Both excision and inversion within the recombination site occur as a result of homologous recombination through the site-specific recombination system, which is different from the mechanism using the transposon. It is known that the recombinase gene is not necessarily present in the same DNA molecule, in which the recombination site exist. The recombinase gene only needs to be present in the same cell and expressed to excise or invert the region held by the two DNA sequences (N. L. Craig, *Annu. Rev. Genet.,* 22:77, 1988).

At present, site-specific recombination systems have been identified in microorganisms such as phage, bacterium (e.g., *E. coli*), yeast and the like. Examples thereof include a Cre/lox system, a pSR1 system, a FLP system, a cer system, and a fim system (for example, N. L. Craig, *Annu. Rev. Genet.,* 22:77, 1988). When the site-specific recombination system separated from these microorganisms with the use of a Cre/lox system derived from P1 phage (International Laid-Open No. WO 93/01283) is introduced into organisms (including plants) different from the organism from which this system had been derived, it behaves in the same way as in the original organism. The site-specific recombination system of yeast (*Zygosaccharomyces rouxii*) (pSR1 system (H. Matsuzaki et al., *J. Bacteriology,* 172:610, 1990)) can also be used in accordance with the present invention. This pSR1 system also maintains its inherent function in higher plants (H. Onouchi et al., *Nucleic Acid Res.,* 19:6373, 1991).

According to the present invention, this removable DNA element is put under control of an inducible promoter.

That is, inducible promoters are present in upstream of structural genes in all organisms ranging from prokaryotic organisms (for example, bacteria and the like) to eucaryotic organisms (for example, yeasts, fungi, higher plants, mammals and the like), and these elements control expression of a certain gene or a group of genes by functioning alone or in concert with one another. For example, they carry out on/off of the gene expression sometimes in response to the stage of differentiation and growth of each individual or occasionally depending on the heat, light, metals and the like environmental factors. According to the present invention, an inducible promoter having such functions is used, and a removable DNA element positioned in its downstream controls expression, or removability.

Examples of such inducible promoters so far known include those which respond to chemical substances, such as glutathione-S-transferase I system gene promoter (Unexamined Published Japanese Patent Application No. H05-268965), glutathione-S-transferase II system (GST-II) gene promoter (International Laid-Open No. WO 93/01294), Tet repressor fusion type cauliflower mosaic virus 35S promoter (C. Gatz et al., *Mol. Gen. Genet.,* 227:229, 1991), Lac operator/repressor system promoter (R. J. Wilde et al., *The EMBO Journal,* 11:1251, 1992), alcR/alcA system promoter (International Laid-Open WO 94/03619), glucocorticoid system promoter (Takushi Aoyama, *Protein, Nucleic acid and Enzyme,* 41:2559, 1996) and the like, those which respond to heat, such as hsp80 promoter (Unexamined Published Japanese Patent Application No. H05-276951) and the like and those which respond to light, such as ribulose-bisphosphate carboxylase small subunit gene (rbcS) promoter (R. Fluhr et al., *Proc. Natl. Acad. Sci. USA,* 83:2358, 1986), fructose-1,6-bisphosphatase gene promoter (Japanese Domestic Re-publication of PCT International Publication for Patent Application No. H07-501921), light-harvesting chlorophyll a/b binding protein gene promoter (Unexamined Published Japanese Patent Application No. H05-89) and the like.

Among these promoters, the rbcS promoter has been studied most progressively as an inducible promoter in higher plants and analyzed more in detail by Chua et al. (for example, see Matsuoka, *Plant Cell Technology Supplement,* 3:552, 1991). Because of this reason, this promoter was used in Example 1 of the present invention, but the mechanism of this factor in regulating gene expression in response to light has not been established yet. On the other hand, promoters which respond to chemical substances, typically including the GST-II gene promoter, can control induction of gene expression relatively freely in response to the amount of chemical substances, so that they have an advantage in practical use in comparison with heat- or light-responding promoters which have to control gene expression by controlling heat or light.

In the present invention, the morphological abnormality induction gene may be inserted into a position where this gene is excised along with the removable DNA element. For instance, when the transposon is used as the removable DNA element, the morphological abnormality induction gene can be inserted into a position which does not influence the excision of the transposon and which is upstream of the promoter region of the transposase gene but downstream of the terminal region to which the transposase binds. When the pSR1 system is used, the morphological abnormality induction gene can be inserted into any position within the region held by the recombination sites which does not inhibit the expression of the recombinase.

The vector of the present invention can be used in any plants into which the gene can be introduced by genetic engineering methods. The desired gene in accordance with the present invention can be any gene by which agriculturally excellent characteristics can be imparted and any gene which allows for studies of gene expression mechanisms and the like, though agriculturally excellent characteristics are not necessarily imparted.

With regard to a promoter and a terminator for the desired gene, they can be used without any restrictions so long as they function in plants. Examples of promoter include the 35S promoter of a cauliflower mosaic virus (J. T. Odell et al., *Nature* (London), 313:810, 1985), the promoter of a nopaline synthetase (W. H. R. Langridge et al., *Plant Cell Rep.,* 4:355, 1985), and the like. Examples of terminator include the polyadenylation signal of a nopaline synthetase (A. Depicker et al., *J. Mol. Appl. Gen.,* 1:561, 1982), the polyadenylation signal of an octopine synthetase (J. Gielen et al., *EMBO J.,* 3:835, 1984), and the like.

Furthermore, the gene, that is, DNA, of the present invention can be obtained by cloning cDNA or genomic DNA, or by chemical synthesis if its sequence is known.

The vector of the present invention can be indirectly introduced into the plant cell through viruses or bacteria with which plants are infected (I. Potrykus, *Annu. Rev. Plant Physiol. Plant Mol. Biol.,* 42:205, 1991). Examples of viruses include cauliflower mosaic virus, geminivirus, tobacco mosaic virus, brome mosaic virus, and the like. Examples of bacteria include *Agrobacterium tumefaciens* (hereinafter referred to as *A. tumefaciens*), *Agrobacterium rhizogenes*, and the like. Dicotyledonous plants are generally known to be infected with the bacteria of the genus Agrobacterium. Recently, the introduction of genes into the monocotyledonous plants by the infection of these plants with them has also been reported (for example, International Laid-Open No. WO 94/00977).

The vector of the present invention can be directly introduced into the plant cell by physical and chemical methods such as a microinjection, an electroporation, a polyethylene glycol method, a fusion method, a high-speed ballistic penetration, and the like (I. Potrykus, *Annu. Rev. Plant Physiol. Plant Mol. Biol.,* 42:205, 1991). Since the general indirect introduction method using the genus Agrobacterium cannot be applied to many of the monocotyledonous plants and the dicotyledonous plants which are resistant to infection with Agrobacterium, the above-mentioned direct introduction methods are effective for these plants.

[Effects]

In the present invention, the morphological abnormality induction gene is expressed to make the cell physiological abnormal. Physiological abnormalities include the production of plant growth hormone in a plant cell, with the result that the proliferation and differentiation of the cell containing the morphological abnormality induction gene are confused to induce various morphological abnormalities. For example, an aggregate of disordered shoots with the apical dominance destroyed (extreme shooty phenotype), hairy roots or the like, can be derived from a cell into which such a morphological abnormality induction gene is introduced. This phenotype is formed by abnormal proliferation and differentiation of the above-mentioned cell. Thus, this morphologically abnormal tissue is made up only of the cell containing this gene. Accordingly, if the vector is constructed using this gene as the selectable marker gene together with the desired gene and is introduced into the plant cell and the cell is cultured, the tissue made up only of the cell into which the selectable marker gene and the desired gene have been introduced can be selected by merely visually selecting the morphologically abnormal tissue derived from the plant cell.

Furthermore, according to the present invention, the morphological abnormality induction gene is used by incorporating it into a position where it behaves integrally with the removable DNA element which is put under control of an inducible promoter. When a gene is introduced into a plant by using a vector having such a construction, the removable DNA element can be expressed by artificially applying an appropriate stimulus such as heat, light, a chemical substance or the like depending on the used inducible promoter to the plant cells after the gene transfer, so that the morphological abnormality induction gene as a selectable marker gene disappears its function by removing along with this removable DNA element, at a certain ratio from the DNA molecule where they were once introduced and functioned, while the desired gene which does not behave integrally with it remains on the same DNA molecule and maintains its function, thus, in other words, cells in which only the desired gene is introduced can be obtained.

Moreover, since the disappearance of the function of this selectable marker gene, namely the disappearance of the function of the morphological abnormality induction gene, can be visually detected as morphological change of the gene introduced-tissue in the same manner as in the introduction of the gene, the tissue made up only of the cells in which the function of the selectable marker gene has been disappeared, in other words, the tissue made up only of the cells in which only the desired gene is introduced, can be selected surely and easily. That is, in order to obtain the tissue made up only of such cells, the cells after the gene introduction are cultured, the tissue showing morphological abnormality, such as shooty phenotype, hairy roots or the like, caused by the expression of the morphological abnormality induction gene is visually selected, and the selected tissue is separated. Then, if appropriate stimulus is optionally applied thereto according to the used inducible promoter during culturing of the separated tissue, a tissue showing morphological normality is obtained this time from the tissue showing morphological abnormality, and can also be visually selected.

BEST MODE OF CARRYING OUT THE INVENTION

EXAMPLES

Figure 1:
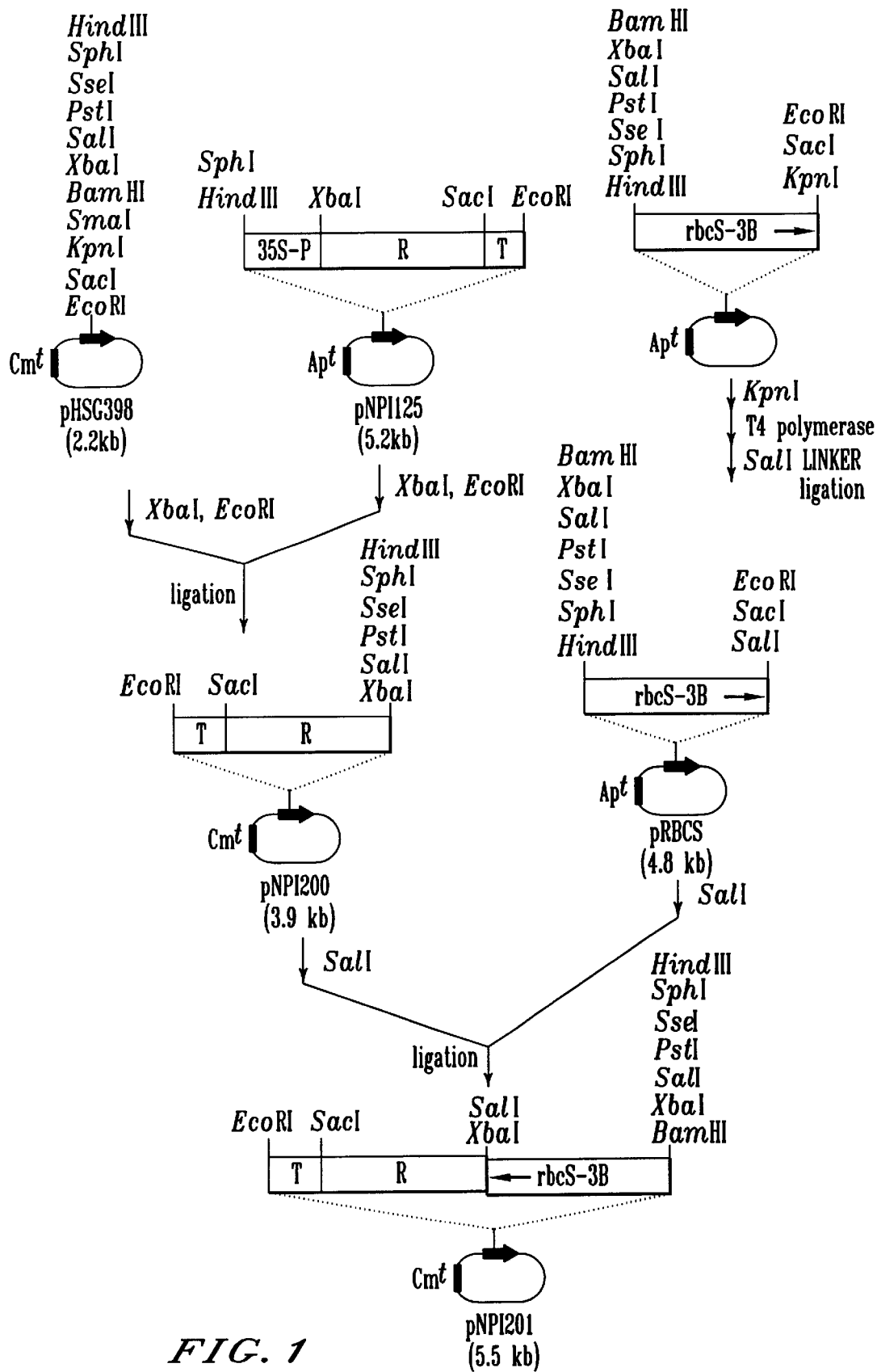
FIG. 1 shows steps until preparation of pNPI201 in the pNPI206 construction scheme.
Figure 2:
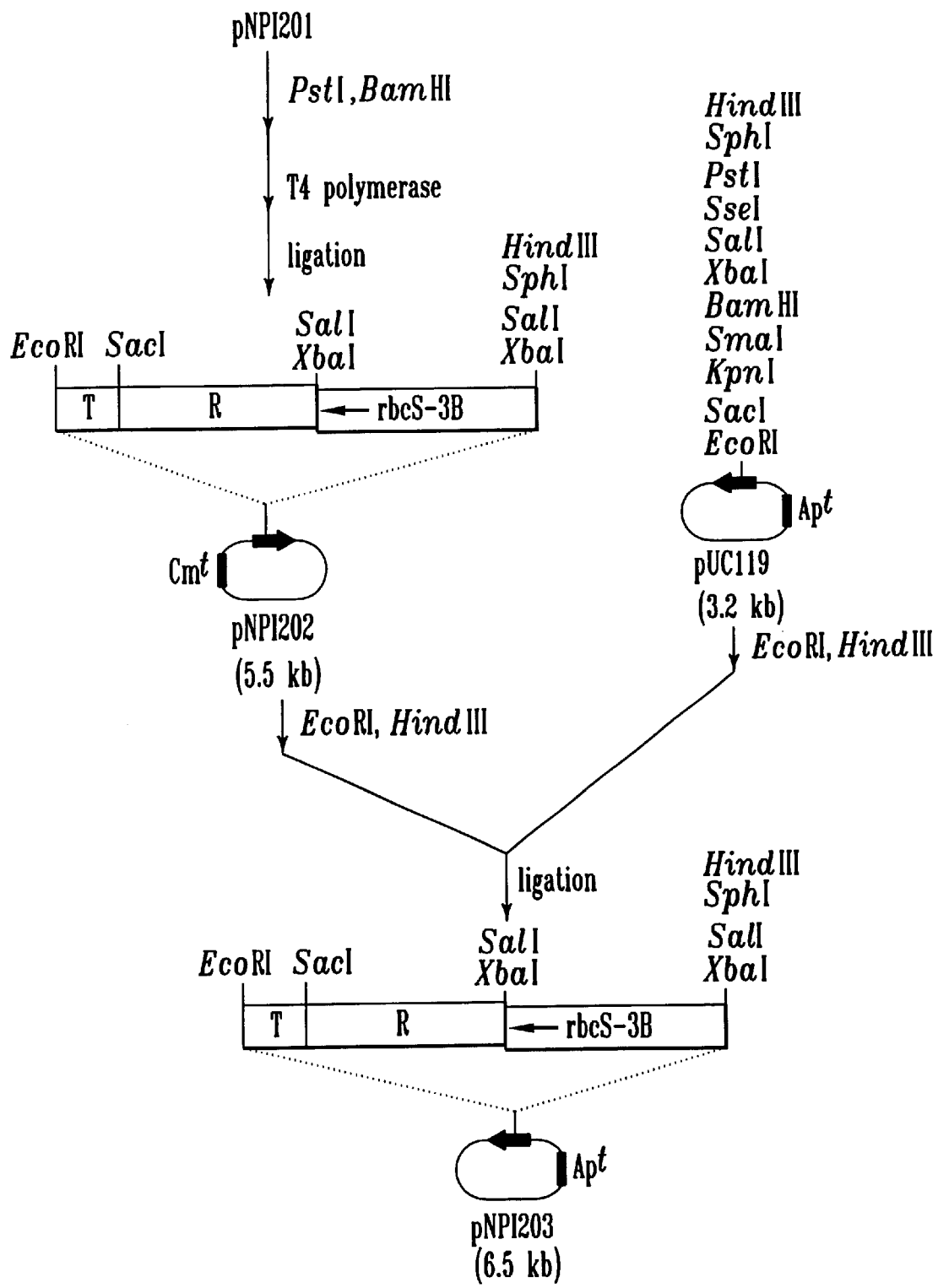
FIG. 2 shows steps for the preparation of pNPI201 to pNPI203 in the pNPI206 construction scheme.
Figure 3:
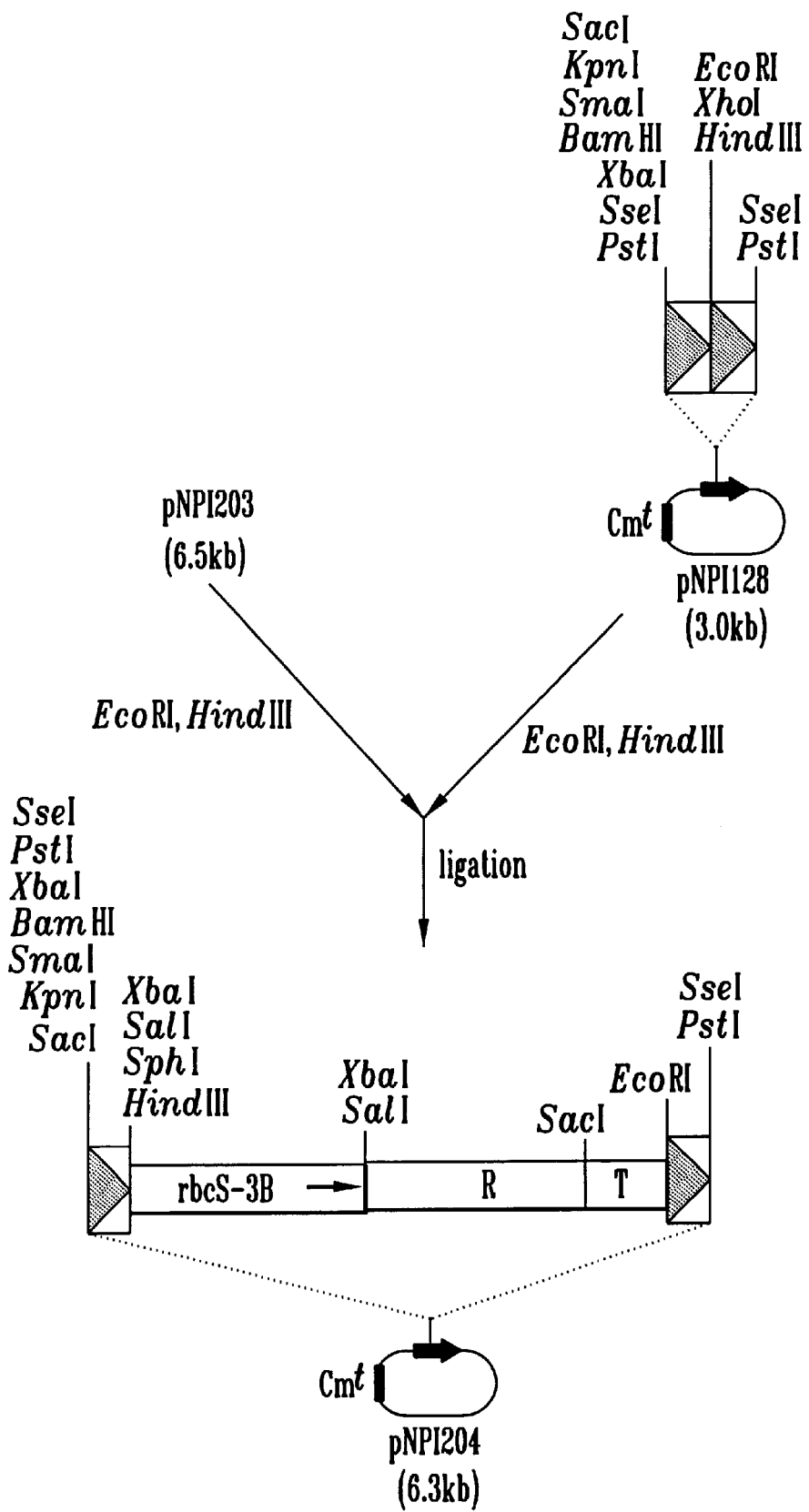
FIG. 3 shows steps for the preparation of pNPI203 to pNPI204 in the pNPI206 construction scheme.
Figure 4:
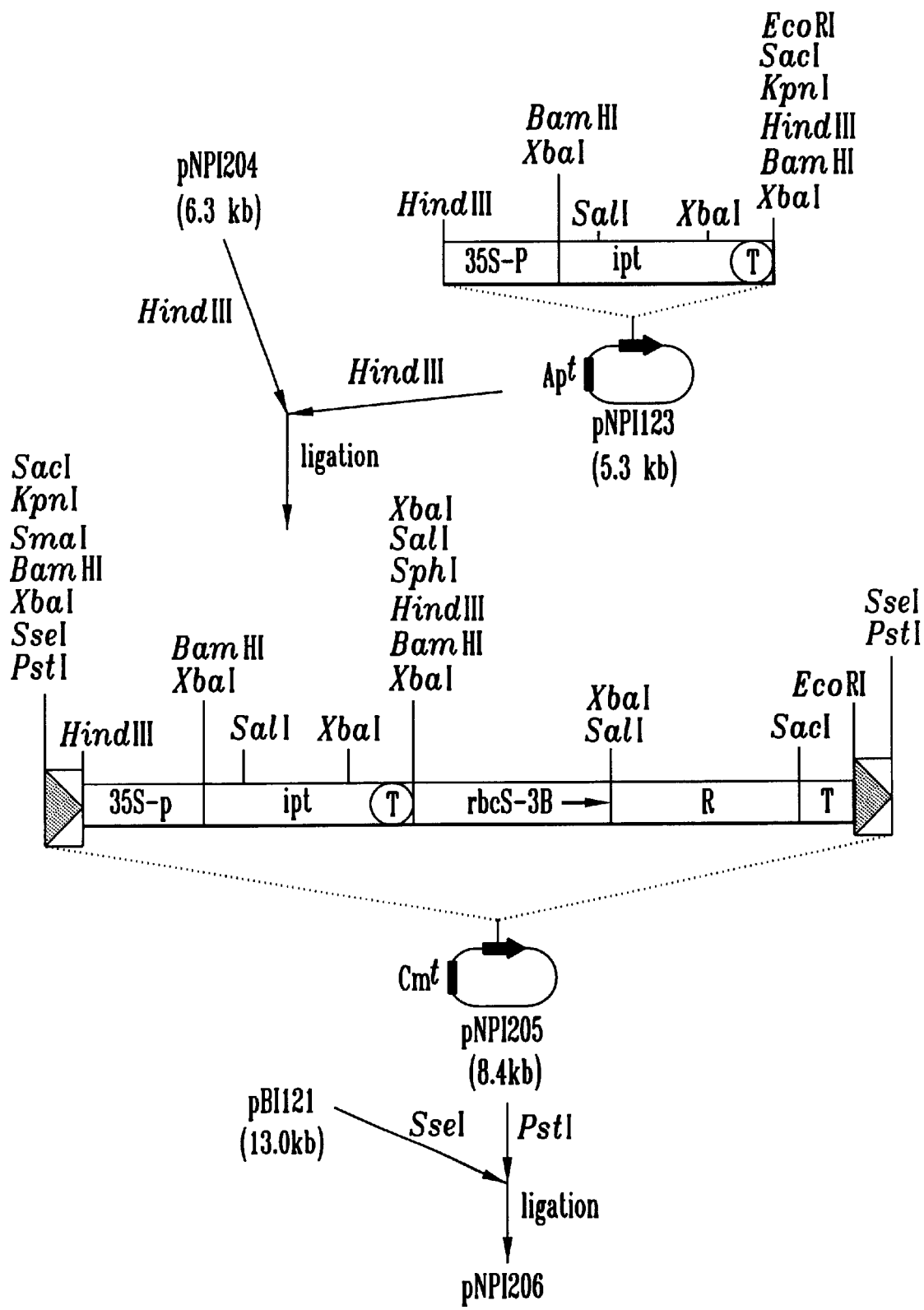
FIG. 4 shows steps for the preparation of pNPI204 to pNPI206 in the pNPI206 construction scheme.

In the following Examples, the experiments were conducted according to the instructions of Molecular Cloning, 2nd edition (Sambrook et al. eds., Cold Spring Harbor Laboratory Press, New York, 1989) or through a manufacturer unless otherwise instructed.

Example 1

1. Construction of Vector

The recombinase gene (hereinafter referred to as "R gene") of a yeast site-specific recombination system (pSR1 system) and the nopaline synthetase polyadenylation signal linked thereto were cut out with restriction endonucleases XbaI and EcoRI from the plasmid pNPI125 described in Japanese Patent Application No. H07-313432 and inserted between the XbaI-EcoRI restriction endonuclease site of pHSG398 (purchased from Takara Shuzo Co., Ltd.) to obtain a plasmid pNPI200.

On the other hand, a plasmid containing the ribulose-bisphosphate carboxylase small subunit gene promoter (rbcS-3B) (obtained from Dr. Mamoru Sugita of Nagoya University) was digested with a restriction endonuclease KpnI, and the cohesive termini thus produced by the digestion were changed into blunt-ended termini with T4 polymerase I (large subunit). Then, 5'-phosphorylated SalI linker was inserted between the resulting blunt-ended termini to obtain a plasmid pRBCS, and the rbcS-3B was cut out from the pRBCS with a restriction endonuclease SalI and inserted into the SalI restriction endonuclease site of pNPI200 to obtain a plasmid pNPI201.

Also, the rbcS-3B is a light-responding promoter derived from a tomato (*Lycopersicon esculentum* VFNTLA 1221).

In addition to this promoter, tomatoes have five other similar promoters (rbcS-1, -2, -3, -3A and -3C) as inducible promoters of rbcS, and their expression modes have been analyzed by Sugita et al. (M. Sugita et al., *Proc. Natl. Acad. Sci. USA*, 84:7104, 1987).

Next, the plasmid pNPI201 was digested with restriction endonucleases PstI and BamHI, and the cohesive termini thus produced by the digestion were changed into blunt-ended termini with T4 polymerase I (large subunit) and then ligated to obtain a plasmid pNPI202. Using restriction endonucleases EcoRI and HindIII, a fragment containing rbcS-3B, R gene and nopaline synthase polyadenylation signal was cut out from the plasmid pNPI202 and inserted between the EcoRI-HindIII restriction endonuclease site of pUC119 (purchased from Takara Shuzo Co., Ltd.) to obtain a plasmid pNPI203, and the fragment containing rbcS-3B, R gene and nopaline synthase polyadenylation signal was again cut out from the plasmid pNPI203 with restriction endonucleases EcoRI and HindIII and inserted between the EcoRI-HindIII restriction endonuclease site of the plasmid pNPI128 described in Japanese Patent Application No. H07-313432 to obtain a plasmid pNPI204.

Thereafter, into the HindIII restriction endonuclease site of the thus obtained plasmid pNPI204 was inserted a fragment containing cauliflower mosaic virus 35S promoter (CaMV35S promoter) and ipt gene connected thereto, which had been cut out from the plasmid pNPI123 also described in Japanese Patent Application No. H07-313432 using the restriction endonuclease HindIII, to obtain a plasmid pNPI205.

The desired vector could be obtained by cutting out fragment containing the ipt gene linked to the CaMV35S promoter, the R gene and nopaline synthase polyadenylation signal linked to the rbcS-3B and the recombination sequence Rs of yeast site-specific recombination system located on both termini thereof from the plasmid pNPI205 with a restriction endonuclease PstI and inserting it into the SseI restriction endonuclease site of a vector plasmid pBI121 for use in gene transfer into plants (purchased from TOYOBO CO., LTD.), and the thus obtained desired vector was named plasmid pNPI206. When a plant is infected with *A. tumefaciens* containing this plasmid, a T-DNA region which exists between an RB site and LB site of the plasmid, in this case, a region of about 12.5 kb from the nptII gene (neomycin phosphorylation enzyme gene) to GUS gene (β-glucronidase gene), is integrated into the plant chromosome.

Also, the plasmid pNPI206 was introduced into *Escherichia coli* JM109 strain, and the resulting strain was applied to international deposition as *E. coli* JM109 (pNPI206) [National Institute of Bioscience and Human Technology, Agency of Industrial Science and Technology, the Ministry of International Trade and Industry (Higashi 1-1-3, Tsukuba-shi, Ibaraki, Japan, 305), international accession number FERM BP-5518, original deposition under Budapest Treaty on Apr. 24, 1996].

Figure 5:
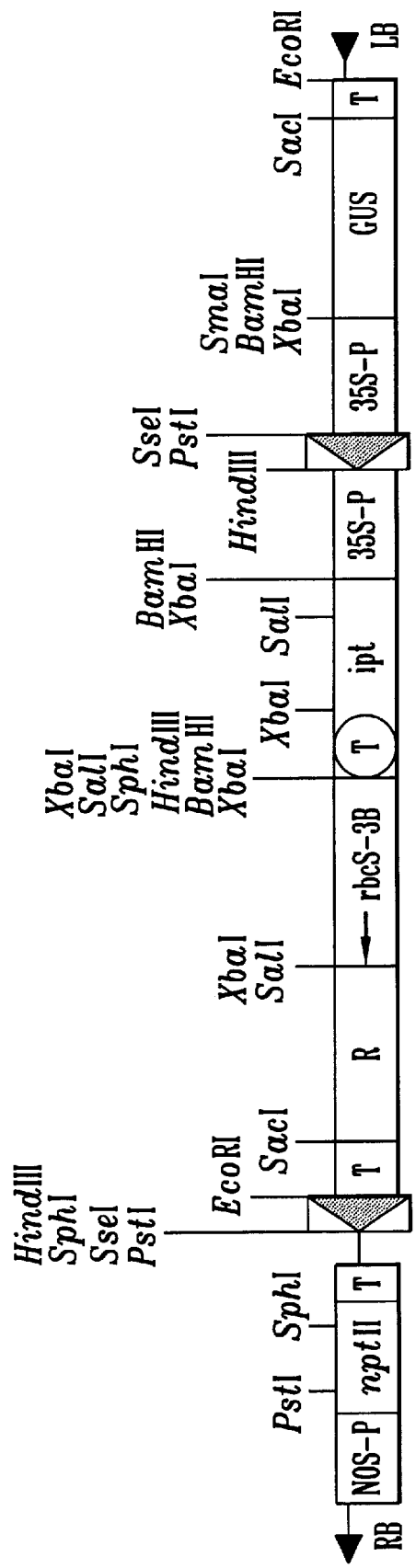
FIG. 5 is a restriction enzyme map of the T-DNA region in the pNPI206 structure.
Figure 6:
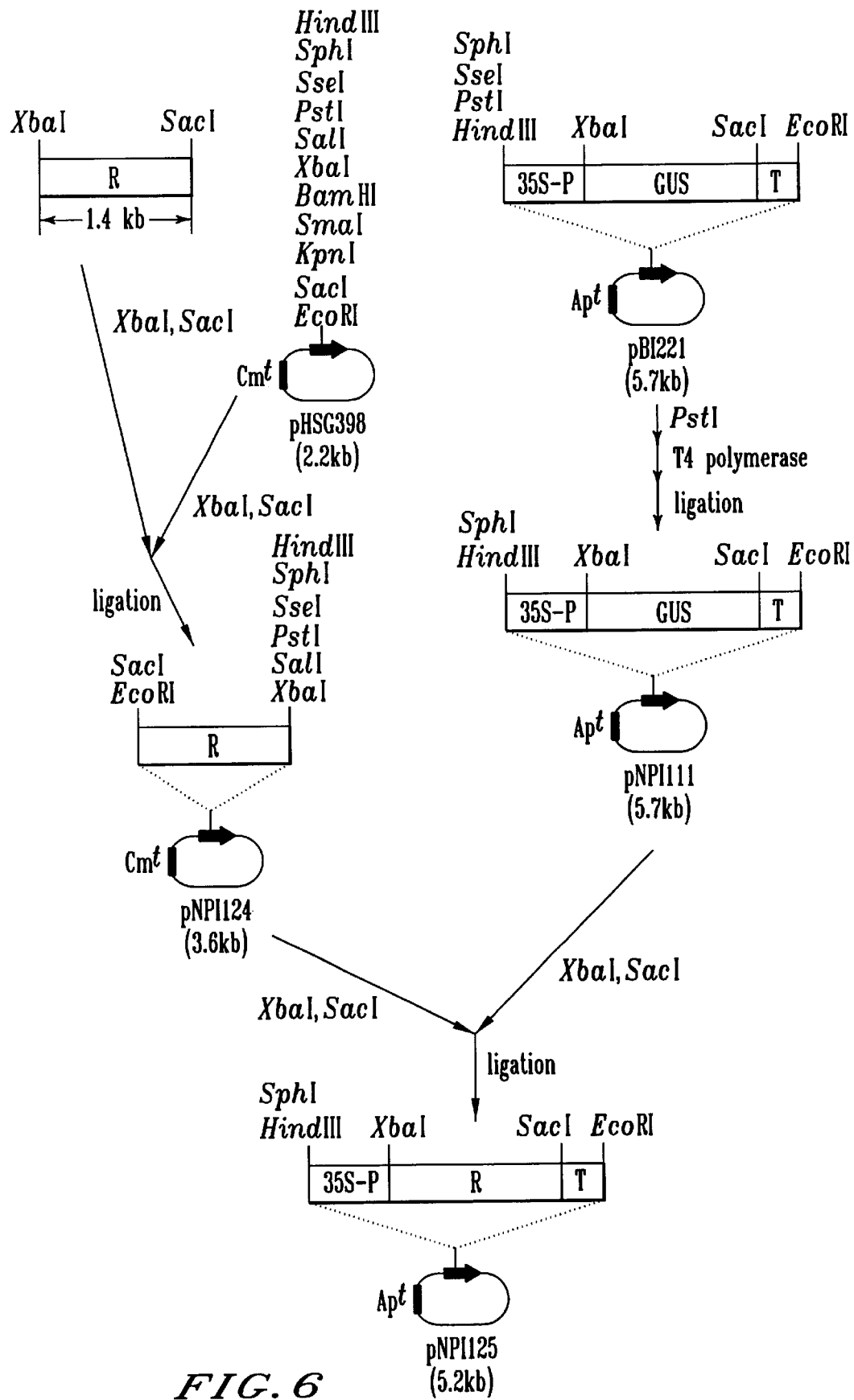
FIG. 6 shows construction scheme of pNPI125.
Figure 7:
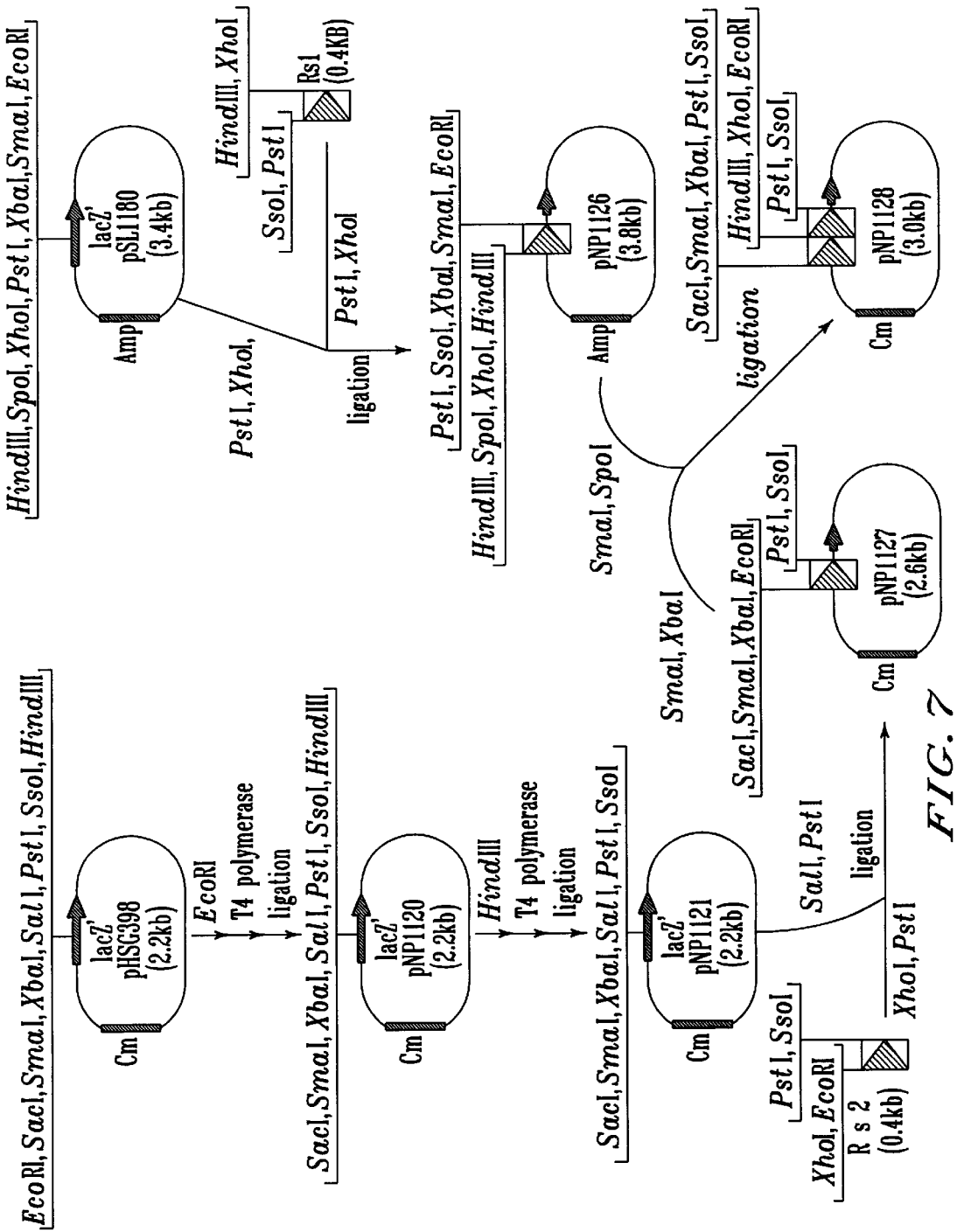
FIG. 7 shows construction scheme of pNPI128.
Figure 8:
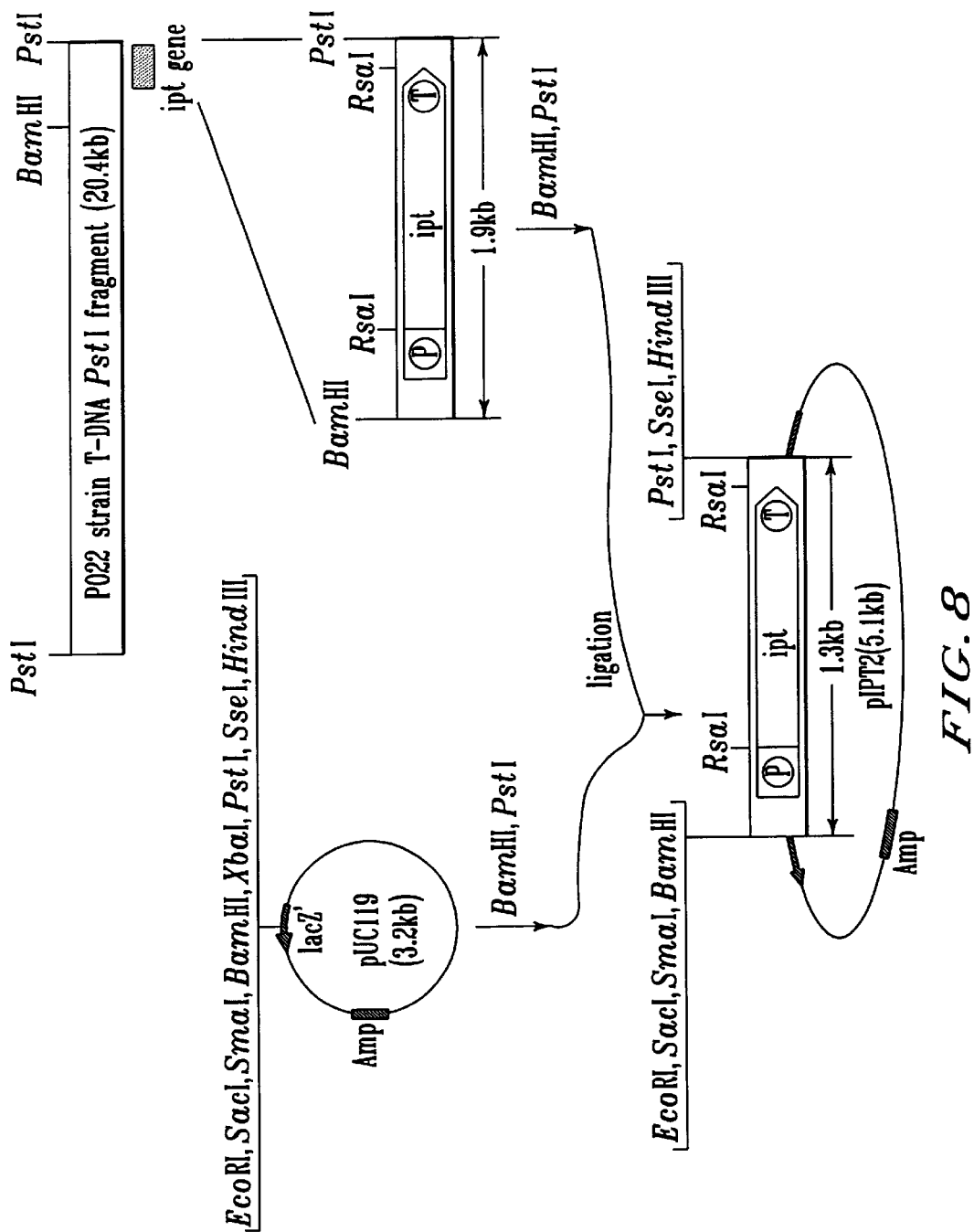
FIG. 8 shows steps until preparation of pIPT2 in the pNPI123 construction scheme.
Figure 9:
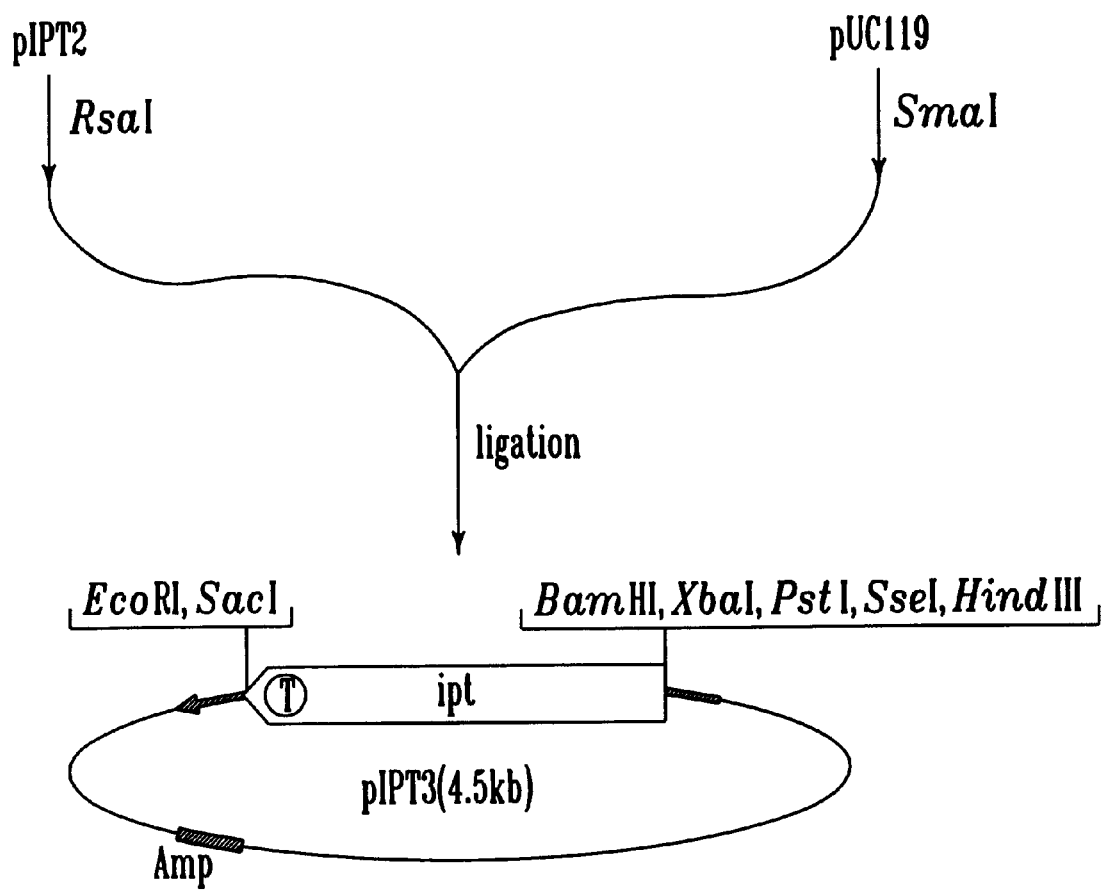
FIG. 9 shows steps for the preparation of pIPT2 to pIPT3 in the pNPI123 construction scheme.
Figure 10:
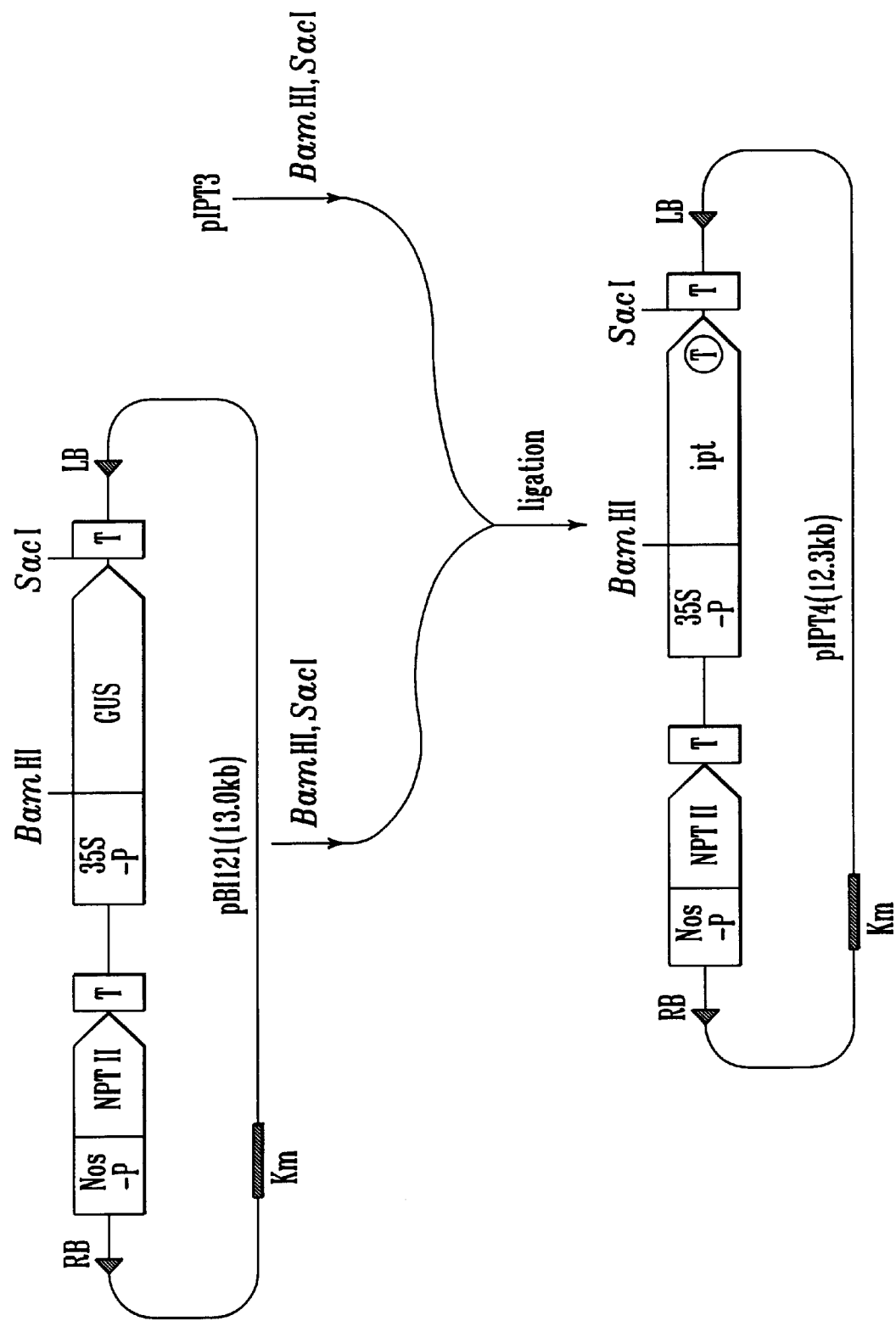
FIG. 10 shows steps for the preparation of pIPT3 to pIPT4 in the pNPI123 construction scheme.
Figure 11:
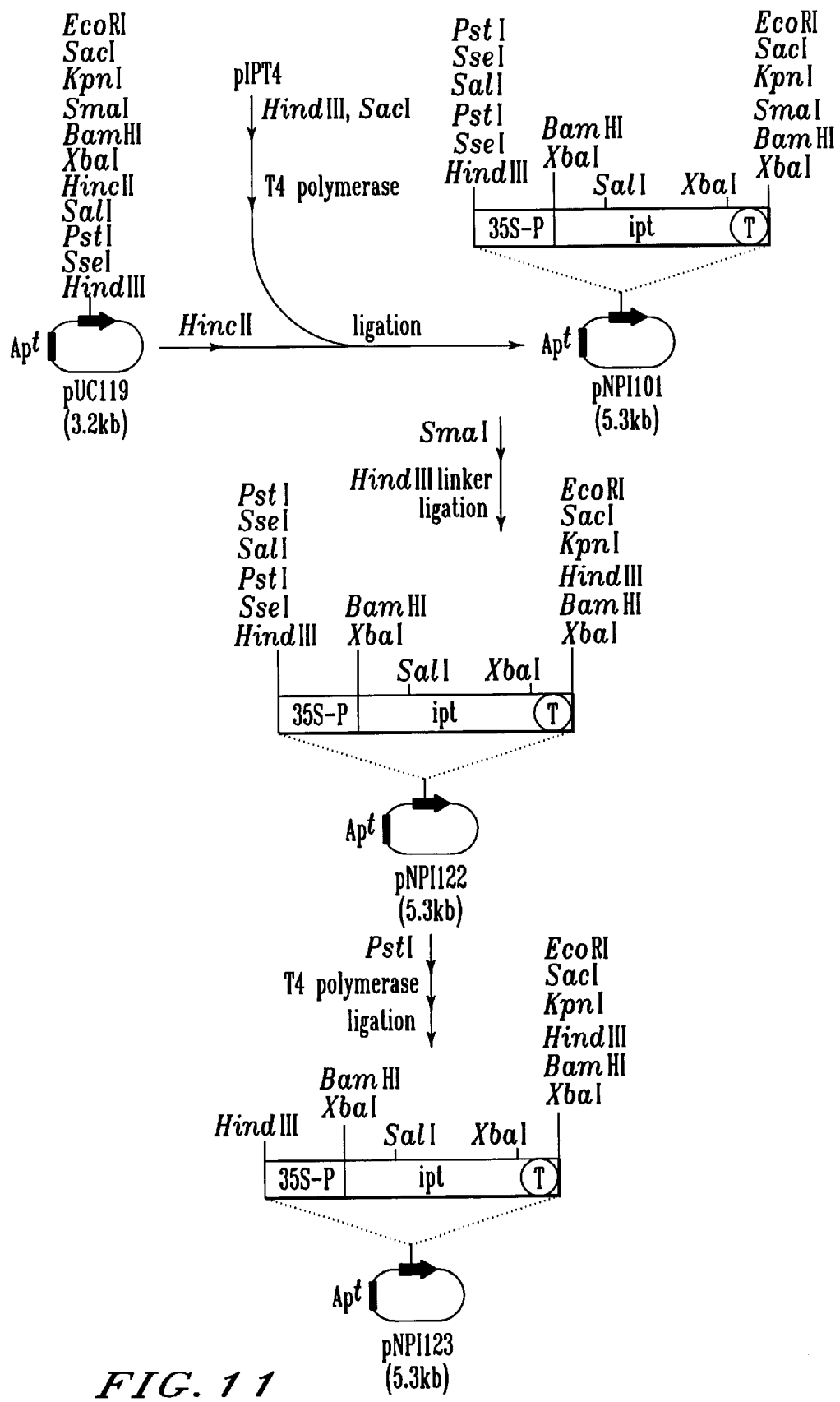
FIG. 11 shows steps for the preparation of pIPT4 to pNPI123 in the pNPI123 construction scheme.
Figure 12:
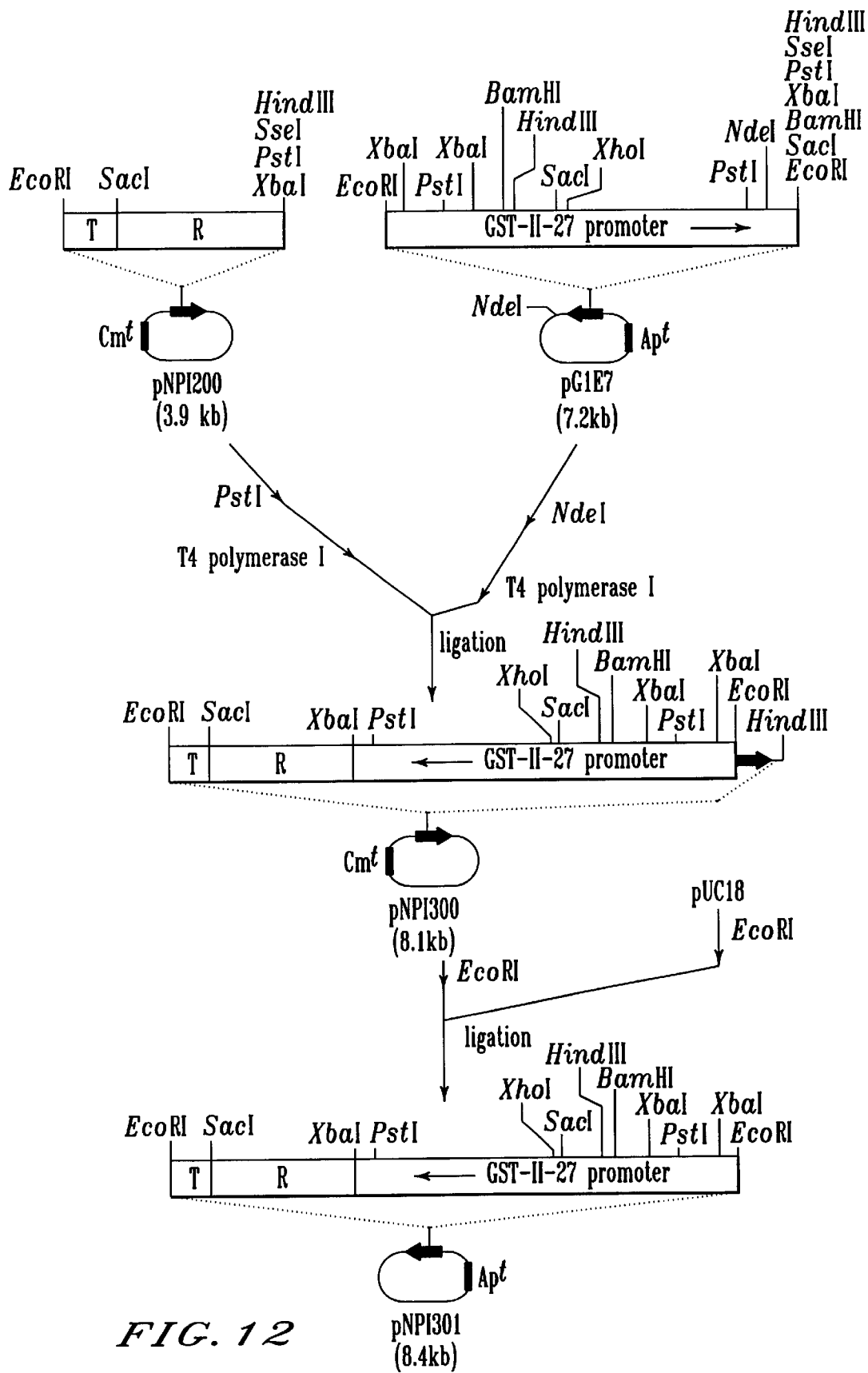
FIG. 12 shows steps for the preparation of pNPI200 and pG1E7 to pNPI301 in the pNPI303 construction scheme.
Figure 13:
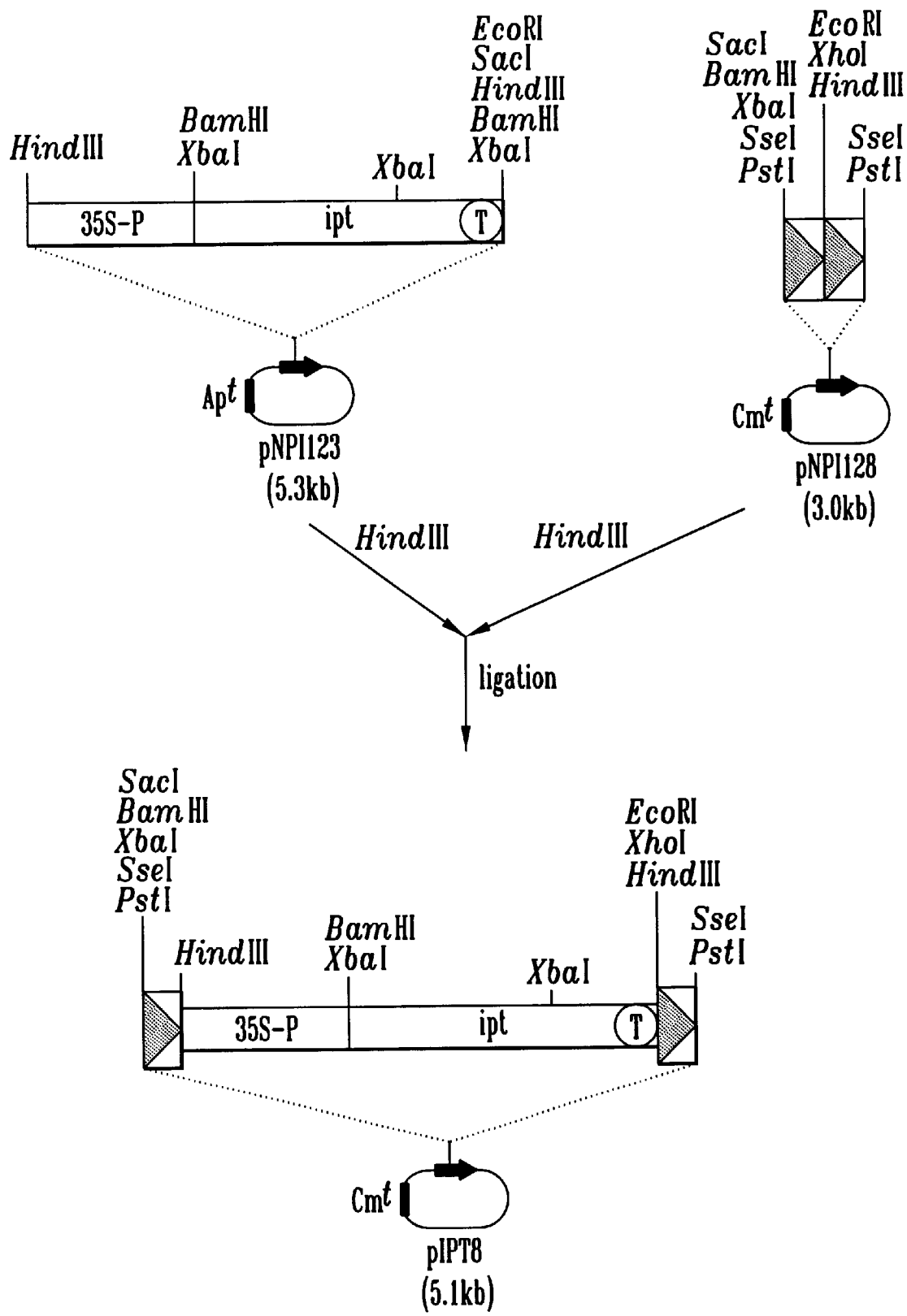
FIG. 13 shows steps for the preparation of pNPI123 and pNPI128 to pIPT8 in the pNPI303 construction scheme.
Figure 14:
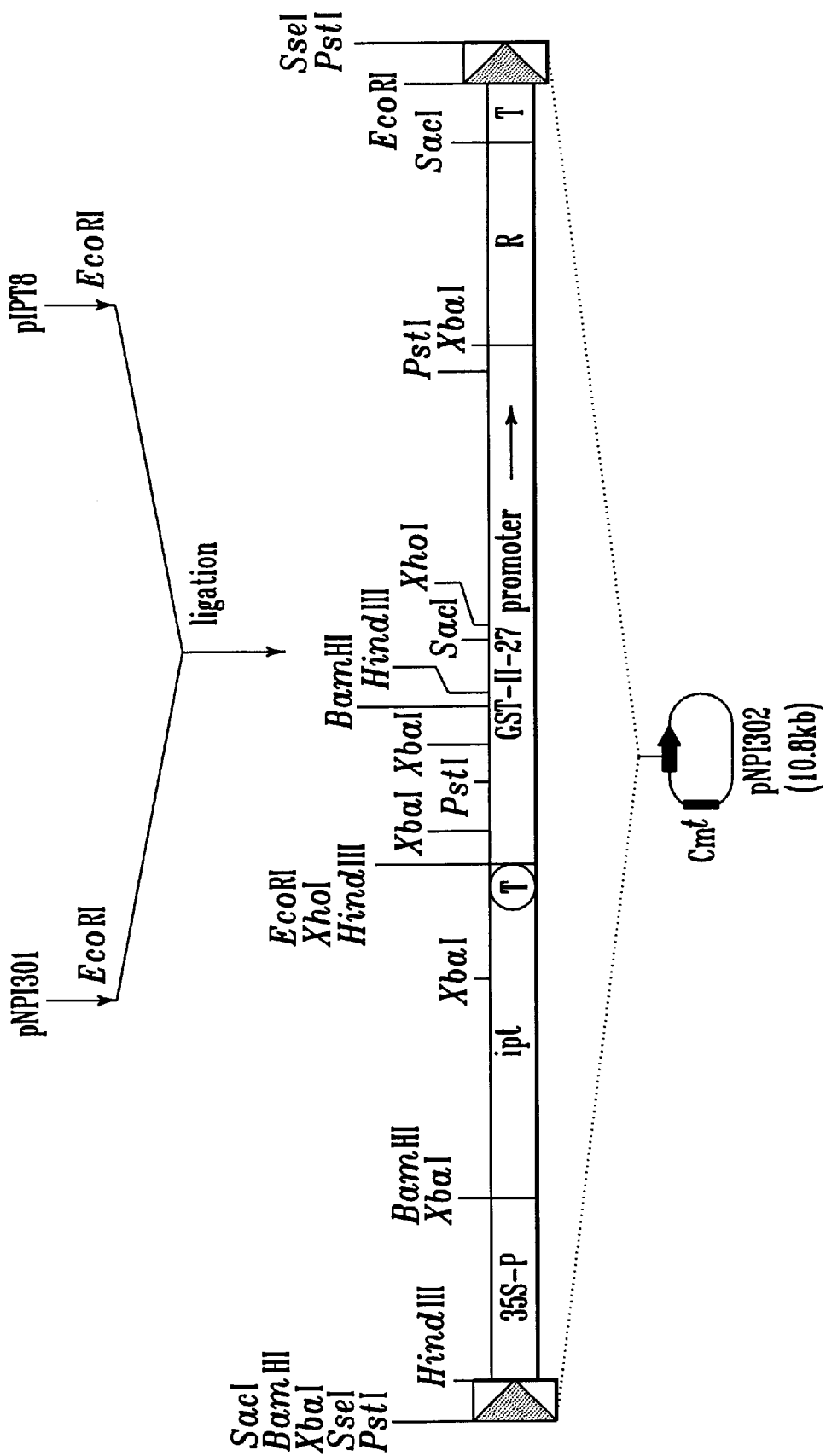
FIG. 14 shows steps for the preparation of pNPI301 and pIPT8 to pNPI302 in the pNPI303 construction scheme.
Figure 15:
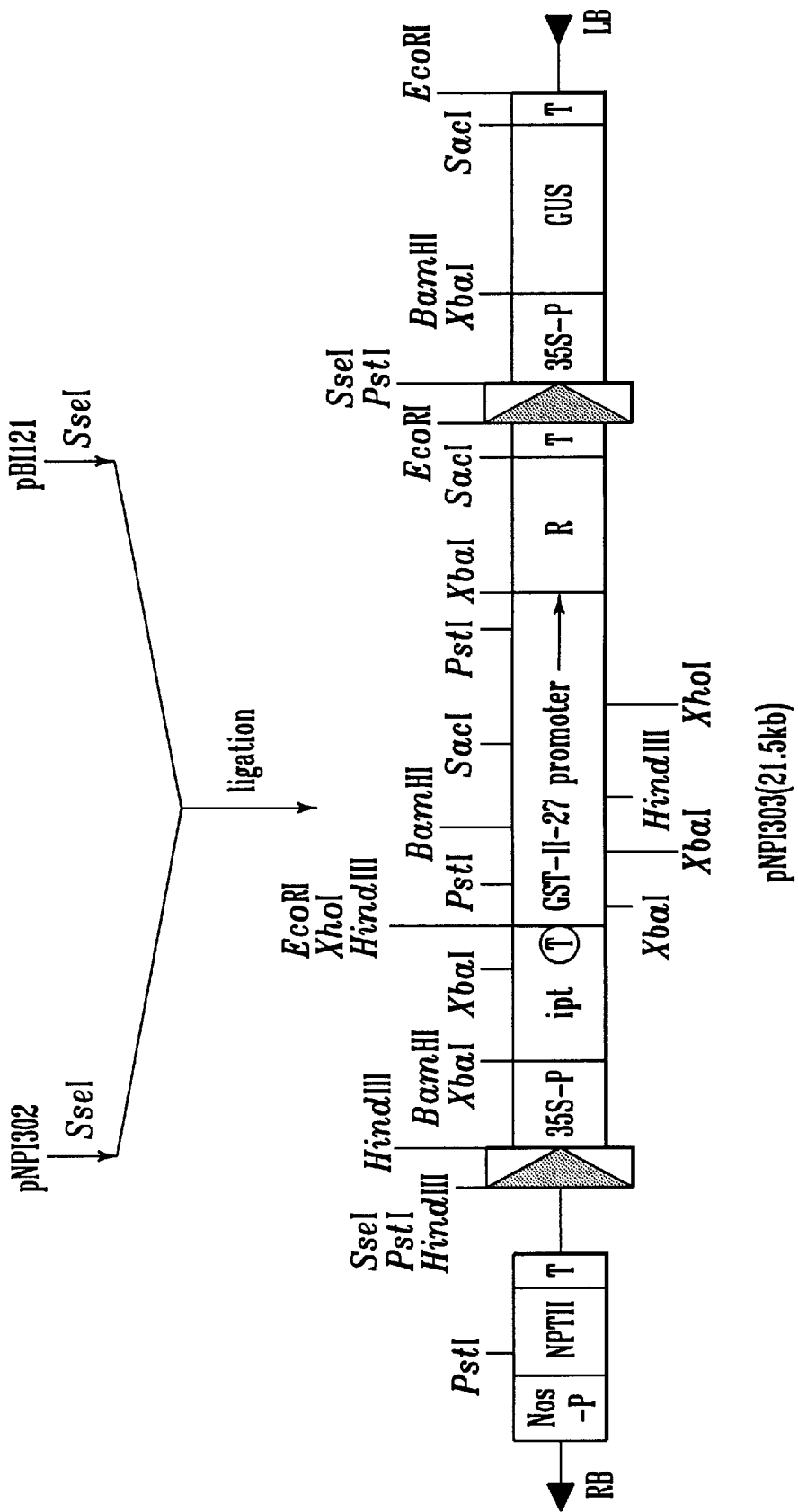
FIG. 15 shows steps for the preparation of pNPI302 to pNPI303 in the pNPI303 construction scheme.

The construction scheme of pNPI206 is shown in FIGS. 1 to 4 and the restriction endonuclease map of its T-DNA region is shown in FIG. 5. Also, the construction scheme of pNPI125 is shown in FIG. 6, the construction scheme of pNPI128 is shown in FIG. 7, and the construction scheme of pNPI123 is shown in FIGS. 8 to 11. In these drawings, "35S-P" represents cauliflower mosaic virus 35S promoter, "NOS-P" represents nopaline synthase promoter, "T" represents nopaline synthase polyadenylation signal, "encircled T" represents polyadenylation signal of ipt gene itself, and "triangle of half-tone dot meshing" represents recombination sequence Rs and its sequencing direction.

As apparent from FIG. 5, this plasmid contains the ipt gene as a selectable marker gene and the nptII gene and GUS gene as models of the desired gene in the T-DNA region, namely a region to be integrated into the plant chromosome. This ipt gene is a member of tumor-inducing genes possessed by the pathogenic *A. tumefaciens*, and its introduction into plant cells induces over production of a plant hormone, cytokinin, and differentiation of the resulting cells is directed toward extreme shooty formation. Also, both of the nptII gene which contributes to kanamycin resistance and the GUS gene that produces a blue pigment in cells containing the gene by metabolizing a specific substrate are genes generally used in the analysis of gene expression in plants.

In addition, since a region between a pair of recombination sequence Rs's of a yeast site-specific recombination system (pSR1 system) functions as the removable DNA element in this plasmid, the ipt gene is inserted in such a form that it is sandwiched by the set of the recombination sequence Rs's having the same direction. At the same time, however, the R gene as a gene of an enzyme which catalyzes removing of the region between Rs's is connected to downstream of an inducible promoter, namely the light-responding promoter rbcS-3B, so that the gene is not expressed by regulation of the promoter, or the removing between Rs's does not occur, unless it is put under appropriate light conditions.

II. Introduction of pNPI206 into Agrobacterium

*A. tumefaciens* strain LBA4404 (purchased from CLONTECH CO., LTD.) was inoculated into 10 ml of YEB liquid culture medium (containing 5 g/l of beef extract, 1 g/l of yeast extract, 1 g/l of peptone, 5 g/l of sucrose, and 2-mM $MgSO_4$, pH of 7.2 at 22° C. (the pH at 22° C. is applied to the following unless otherwise instructed)), and was cultured at 28° C. until $OD_{630}$ was within the range of 0.4 to 0.6. Then, the culture was centrifuged at 6,900×g for 10 minutes at 4° C. to collect the cells. The cells were suspended in 20 ml of 10-mM Tris-HCl (pH 8.0), and the suspension was recentrifuged at 6,900×g for 10 minutes at 4° C. Subsequently, the collected cells were resuspended in 200 μl of YEB liquid culture medium, and this suspension was used as a cell suspension for plasmid introduction.

Introduction of pNPI206 into Agrobacterium was carried out by mixing 200 μl of the cell suspension for plasmid introduction with 6 μg of the pNPI206 obtained in the above-described step I in a 15 ml capacity tube (manufactured by Falcon), cooling the mixture by soaking the tube for 5 minutes in ethanol which had been cooled in advance for 30 to 40 minutes in liquid nitrogen, putting the tube for 25 minutes in a water bath of 29° C., adding 750 μl of YEB liquid medium to the tube and then culturing the cells in the tube at 29° C. for 1 hour on a shaker.

III. Introduction of pNPI206 from Agrobacterium into Tobacco, Culturing of pNPI206-introduced Tobacco Cells and Morphology of the Obtained Tissue Matured leaves of a tobacco (*Nicotiana tabacum* cv. SR1) grown in a greenhouse were dipped in a 1 v/v% sodium hypochlorite aqueous solution for sterilization, and washed three times with sterile water. Then, the midrib of the leaf was removed to form leaf discs of approximately 8 mm square. The thus-obtained leaf discs were then dipped for approximately 1 minute in a cell suspension of *A. tumefaciens* strain LBA4404 introduced pNPI206 in the above-described step II, and was infected therewith (which suspension was diluted with a sterilized water at $OD_{630}$=0.25 after the overnight culturing in YEB liquid culture medium). The infected leaf disc was put on a sterilized filter paper to remove any extra cell suspension. Then, it was laid on hormone-free MS agar culture medium (T. Murashige and F. Skoog, Physiol. Plant., 15:473, 1962 (provided that 0.8 w/v% agar was added thereto)) containing 50 mg/l of acetosyringone with the back of the leaf facing upward, and was cultured for 3 days, at 25° C. in a dark place (hereinafter, culturing temperature of a plant tissue was 25° C. unless otherwise instructed). Next, when this was transplanted into hormone-free MS agar culture medium containing only 500 mg/l of carbenicillin and cultured under a quantity of light of approximately 7 to 10 $\mu$mol s$^{-1}$m$^{-2}$ while subculturing with the medium having the same components, 225 extreme shooty phenotype lines were obtained after 3 months of the infection, so that 126 lines among them were divided into two groups and culturing of each group was continued under a quantity of light of approximately 7 to 10 $\mu$mol s$^{-1}$m$^{-2}$ or of approximately 70 $\mu$mol s$^{-1}$ m$^{-2}$ using the medium having the same components.

As the results, shoots having normal morphology visually (hereinafter referred to as a "normal individual") were generated from 43 extreme shooty phenotype lines after about 6 months of the infection in the lines cultured under a quantity of light of approximately 70 $\mu$mol s$^{-1}$m$^{-2}$, while only 12 extreme shooty phenotype lines generated normal individuals after the same period of time in the lines cultured under a quantity of light of approximately 7 to 10 $\mu$mol s$^{-1}$m$^{-2}$.

The results are shown in Table 1.

TABLE 1

Light conditions and generation ratio of normal individuals in cultured tobacco tissue transformed with pNPI206

| Light conditions*[1] | The number of extreme shooty phenotype lines used for the examination of light conditions | The number of lines which generated normal individuals | Generation ratio of normal individuals (%)*[2] |
| --- | --- | --- | --- |
| L2 → L1 | 126 | 43 | 34.1 |
| L2 → L2 | 126 | 12 | 9.5 |

Three months of culturing under L2 condition and then three months of culturing under L1 or L2 condition
*[1]Light conditions
L2; a quantity of light of approximately 7 to 10 $\mu$mol s$^{-1}$m$^{-2}$
L1; a quantity of light of approximately 70 $\mu$mol s$^{-1}$ m$^{-2}$
*[2](the number of lines which generated normal individuals/the number of extreme shooty phenotype lines used for the examination of light conditions) × 100

As apparent from the results shown in the above table, when the cultured tobacco tissue transferred with the vector pNPI206 of the present invention is cultured under low light conditions and then cultured under high light conditions, the normal individual generation ratio becomes almost 4 times higher than that of continued culturing under the low light conditions. Accordingly, it is shown that behavior of the morphological abnormality induction gene used as a selectable marker gene is controlled by the light responding promoter rbcS-3B used in the regulation of the removable DNA element, in the gene-introduced tissue using pNPI206, and that its removing is accelerated by shifting light conditions of the gene-introduced tissue from low light quantity to high light quantity.

Example 2

1. Construction of Vector

The plasmid pNPI200 obtained in Example 1 was digested with PstI, and the cohesive termini thus produced by the digestion were changed into blunt-ended termini with T4 polymerase I (large subunit). The GST-II 27 kD subunit gene (GST-II-27) promoter (Japanese Domestic Re-publication of PCT International Publication for Patent Applications No. H06-511385, lines 15 to 17 in the right-side lower column on page 7), which had been cut out from plasmid pG1E7 (obtained from Zeneca Limited) with a restriction endonuclease NdeI and also subjected to blunt-ending of its resulting cohesive termini with T4 polymerase I (large subunit) was subsequently inserted between the blunt-ended termini of pNPI200 to obtain a plasmid pNPI300. Next, a fragment containing the GST-II-27 promoter, R gene and nopaline synthase polyadenylation signal was cut out from the thus obtained pNPI300 with a restriction endonuclease EcoRI and inserted into the EcoRI restriction endonuclease site of pUC18 (purchased from Takara Shuzo Co., Ltd.) to obtain a plasmid pNPI301.

GST-II is an enzyme which exists in corn and the like and is one of the isozymes of GST that concerns in the herbicide detoxification. Also, the GST-II-27 promoter controls gene expression of the 27 kD subunit as one of the GST-II subunits, and it is known that this promoter dramatically increases the GST-II activity to improve resistance of corn and the like against herbicides, by inducing expression of GST-II-27 in the presence of a herbicide antidote, such as 2,2,5-trimethyl-3-(dichloroacetyl)-1,3-oxazolidine or analogs thereof (Japanese Domestic Re-publication of PCT International Publication for Patent Applications No. H06-511385).

On the other hand, CaMV35S promoter and ipt gene linked thereto were cut out from the plasmid pNPI123 with a restriction endonuclease HindIII and inserted into the HindIII restriction endonuclease site of the pNPI128 to obtain a plasmid pIPT8. Then, a fragment containing the GST-II-27 promoter, R gene and nopaline synthase polyadenylation signal was cut out from the pNPI301 with a restriction endonuclease EcoRI and inserted into the EcoRI restriction endonuclease site of the thus obtained pIPT8 to obtain a plasmid pNPI302.

The desired vector can be obtained by cutting out a fragment containing the ipt gene linked to the CaMV35S promoter, the R gene and nopaline synthase polyadenylation signal linked to the GST-II-27 promoter and the recombination sequence Rs's of yeast site-specific recombination system located on both termini thereof from the plasmid pNPI302 with a restriction endonuclease SseI and inserting the fragment into the SseI restriction endonuclease site of the vector plasmid pBI121 for introducing a gene into a plant, and the thus obtained desired vector was named plasmid pNPI303. That is, in this plasmid pNPI303, the GST-II-27 promoter was used to control the R gene instead of the rbcS-3B used in pNPI206. Construction scheme of pNPI303 is shown in FIGS. 12 to 15. Symbols used in these drawings are the same as those used in FIGS. 1 to 11.

Furthermore, the plasmid pNPI303 was also introduced into *Escherichia coli* JM109 strain, and the resulting *Escherichia coli* was applied to international deposition as *E. coli* JM109 (pNPI303) [National Institute of Bioscience and Human Technology, Agency of Industrial Science and Technology, the Ministry of International Trade and Industry (Higashi 1-1-3, Tsukuba-shi, Ibaraki, Japan, 305), international accession number FERM BP-5927, original deposition under Budapest Treaty on Apr. 23, 1997].

II. Introduction of pNPI303 into Tobacco and Analysis of pNPI303-introduced Tobacco In the same manner as described in steps II and III of Example 1, plasmid pNPI303 was introduced into *A. tumefaciens* strain LBA 4404, a leaf disc of tobacco was infected with the resulting *A. tumefaciens* strain LBA 4404 and then thus infected leaf disc was laid on the hormone-free MS agar medium containing 50 mg/l of acetosyringone and cultured for 3 days under light. Next, when the resulting infected leaf was transplanted on the hormone-free MS agar medium containing only 500 mg/l of carbenicillin and the culturing was continued while subculturing with the same medium, extreme shooty phenotypes were obtained, so that 30 lines of these extreme shooty phenotypes obtained after 2 months of the culturing were divided into four groups and each of them was put on the hormone-free MS agar medium containing 500 mg/l of carbenicillin, to which 0, 10, 20 or 30 mg/l of 2,2,5-trimethyl-3-(dichloroacetyl)-1,3-oxazolidine was further added, to examine a generation ratio of normal individuals.

The results after one month of the culturing in the presence of 2,2,5-trimethyl-3-(dichloroacetyl)-1,3-oxazolidine are shown in Table 2. In this case, detection of normal individuals was carried out visually, and a GUS activity test was carried out in accordance with the method of Jefferson et al. in order to confirm expression of the GUS gene used as a model of the desired gene in the example.

On the other hand, expression of the GUS activity, namely the presence and expression of the desired gene, was confirmed in about half of the shoots generated as normal individuals, but the GUS activity was not detectable in the remaining half. Though the reason for this is not yet clear, it is preferred, for example that, if the T-DNA region of pNPI303 is introduced into the tobacco chromosome in the plural by adjoining each other, homologous recombination may occur not between the recombination sequence Rs's within the T-DNA region but between recombination sequences which are present in mutually different T-DNA regions, thus resulting in the removing of the region sandwiched by such sequences. As a result, not only the ipt gene but also the GUS gene could be included in the region which leaves together with the removable DNA element, and, in that case, normal individuals but having no GUS activity would be generated from extreme shooty phenotypes similar to the case of this example.

Also, by subjecting one of the normal individuals which showed the GUS activity to DNA analysis by PCR, the presence of the GUS gene and removing of the ipt gene as a selectable marker gene along with the removable DNA element were confirmed also at the DNA level.

Industrial Applicability

When introduction of a gene into a plant cell is carried out using the vector of the present invention, a selectable marker gene introduced along with the desired gene disappears the function thereof by removing at a certain ratio from the DNA where it exists and functions, caused by the application of specific stimulus, such as heat, light, chemical substance, or the like, to the cell after the gene introduction, and the cell into which the desired gene alone is introduced in such a manner that it can express on the same DNA can be obtained. Accordingly, this vector causes the multiple introduction relating to the gene into a certain plant by merely changing the portion of the desired gene to be introduced

TABLE 2

Generation ratio of normal individuals in cultured tobacco tissue transformed with pNPI303 and concentration of 2,2,5-trimethyl-3- (dichloroacetyl)-1,3-oxazolidine

| The number of normal individuals generated | Concentration 0 (mg/l) | Concentration 10 (mg/l) | Concentration 20 (mg/l) | Concentration 30 (mg/l) |
|---|---|---|---|---|
| The number of lines*[1] | 0 | 5 | 7 | 6 |
| The number of shoots*[2] | 0 (0*[3]) | 5 (2*[3]) | 9 (4*[3]) | 9 (5*[3]) |

One month after the culturing in the presence of 2,2,5-trimethyl-3-(dichloroacetyl)-1,3-oxazolidine
*[1]The number of lines which generated normal individuals
*[2]The number of shoots generated as normal individuals
*[3]The number of individuals among the shoots generated as normal individuals, which showed GUS activity As apparent from the results shown in Table 2, no normal individual was generated when no 2,2,5-trimethyl-3-(dichloroacetyl)-1,3-oxazolidine was added. On the other hand, normal individuals were generated when it was added in an amount of 10 mg/l, and the generation ratio was further increased when it was added in an amount of 20 mg/l. Consequently, it is found also in this case that the GST-II-27 promoter as a chemical substance-responding promoter used in the regulation of a removable DNA element can function properly, so that it induces expression of the removable DNA element and accelerates its removing, and furthermore removing of the morphological abnormality induction gene as a selectable marker gene, when a gene is introduced into a plant tissue by pNPI303 and the resulting tissue is cultured in the presence of an appropriate chemical substance.

without any changing the structures of the selectable marker gene and the others. Thus, the multiple introduction can be conducted an unlimited number of times.

Besides, since a morphological abnormality induction gene was used as the selectable marker gene, the selection of a tissue formed solely from a cell into which the selectable marker gene was introduced, namely a tissue formed solely from a cell into which the desired gene was introduced, as well as the selection of a tissue formed solely from a cell into which the desired gene alone was introduced in such a manner that it can express after the disappearance of the function of the selectable marker gene, can be carried out using morphological change of the tissue as an index. Consequently, a tissue solely derived from a cell in which the desired gene alone is introduced into chromosome or the like can be selected surely and easily, and there is no problem of reducing activities of the plant cell during the selection, because it is not necessary to add antibiotics for selection to the medium. Accordingly, multiple introduction of genes can be carried out efficiently, and a transgenic individual solely composed of such cells, namely an individual from which influences of the selectable marker gene are removed and anxieties about the gene product are completely cleared, can also be obtained without a crossing step.

Moreover, according to the vector of the present invention, removing of the selectable marker gene can be controlled artificially. Consequently, even in the case of a removable DNA element which has markedly excellent removing ability but removes the selectable marker gene so quickly and makes it rather difficult to obtain a tissue solely composed of cells into which a desired gene alone is introduced when such a regulation cannot be conducted, its ability can be used as the removable DNA element of the present invention. On the other hand, since the generation of such cells, as well as the generation of plant tissues composed of such cells, can be optionally synchronized or controlled by using the vector of the present invention, it becomes markedly convenient in actually producing transgenic plants. For example, when the ipt gene is used as a morphological abnormality induction gene which is a selectable marker gene, it induces markedly active growth of a cell into which this gene has been introduced and causes differentiation of adventitious buds and the like under plant hormone-free conditions. Accordingly, a tissue, which can generate a cell into which a desired gene alone is introduced at any time when it is desired, can be produced in a large scale by continuing its culturing rather under its pre-stage condition in which the selectable marker gene is maintained.

What is claimed is:

1. A vector suitable for introducing a gene into a plant, comprising:

a desired gene, a morphological abnormality induction gene which is capable of functioning as a selectable marker gene, and a removable DNA element which is removed by expression of a gene catalyzing the removal, said gene being under the control of an inducible promoter, wherein the morphological abnormality induction gene is present within the removable DNA element, and wherein the desired gene is positioned such that it is not removed together with the removable DNA element.

2. The vector of claim 1, wherein the inducible promoter which controls the removable DNA element is the promoter of ribulose-bisphosphate carboxylase small subunit gene (rbcS).

3. The vector of claim 1, wherein the inducible promoter which controls the removable DNA element is the promoter of glutathione-S-transferase II system (GST-II) gene.

4. The vector of claim 1, wherein the removable DNA element is derived from a site-specific recombination system.

5. The vector of claim 1, wherein the morphological abnormality induction gene is obtained from a bacteria belonging to the genus Agrobacterium.

6. The vector of claim 1, wherein the morphological abnormality induction gene is a cytokinin synthesis gene.

7. The vector of claim 6, wherein the cytokinin synthesis gene is the ipt, isopentenyl transferase, gene which is present in the T-DNA of *Agrobacterium tumefaciens*.

8. The vector of claim 1, wherein the morphological abnormality induction gene induces a morphological change selected from the group consisting of abnormal differentiation, destruction of apical dominance, change in pigments, formation of a crown gall, formation of hairy roots and waving of the leaves.

* * * * *